United States Patent [19]

Helwing

[11] Patent Number: 4,842,868
[45] Date of Patent: Jun. 27, 1989

[54] COVALENTLY BONDED ACTIVE AGENTS WITH CARBONIUM ION BASE GROUPS

[76] Inventor: Robert F. Helwing, 1537 Bedford Ave., Sunnyvale, Calif. 94087

[21] Appl. No.: 912,352

[22] Filed: Sep. 26, 1986

[51] Int. Cl.$^4$ .......................... A61K 9/14; A61F 13/00
[52] U.S. Cl. .................................... 424/486; 424/422; 424/484; 424/59; 424/78
[58] Field of Search .................. 424/468, 486, 59, 78, 424/422, 484

[56] References Cited

U.S. PATENT DOCUMENTS

| | | | |
|---|---|---|---|
| 4,304,767 | 12/1981 | Heller et al. | 424/486 X |
| 4,532,335 | 7/1985 | Helwing | 568/596 X |
| 4,610,870 | 9/1986 | Jain et al. | 424/468 X |

Primary Examiner—Michael R. Lusignan
Attorney, Agent, or Firm—Michael J. Hughes

[57] ABSTRACT

The invention relates to a unique set of compositions of matter characterized by including defined active agents covalently bonded to carbonium ion base groups, as well as the method of creating the compositions. The covalently bonded compositions include base groups in the nature of ketene acetals and vinyl ethers and the thio equivalents thereof. The available active agents include alcohols, phenols, carboxylic acids, thiols, amines, amides, urethanes, phosphate esters, sulfonic acids and oximes. The compositions may either be in capped form or leashed to a polymeric backbone. The compositions are ordinarily formed by self actuating reactions when the appropriate base groups and active agents are juxtaposed under proper environmental conditions. The primary uses of the compositions are in controlled release applications such as drugs, topical insecticides and the like or in any application where predictable hydrolytic release of the active agent is desirable.

45 Claims, No Drawings

COVALENTLY BONDED ACTIVE AGENTS WITH CARBONIUM ION BASE GROUPS

TECHNICAL FIELD

The present invention relates generally to compositions of matter and more particularly to covalently bonded compounds composed of active agents containing reactive functional groups which can combine by leashing or capping with carbonium-ion mechanism type base groups. The present invention is primarily adapted for use with ketene acetal and vinyl ether base groups and their thio-analogs. The primary uses of the invention are in hydrolyzable controlled release utilizations of the active agents in such areas as pharmaceuticals, insecticides, herbicides and the like.

DESCRIPTION OF THE PRIOR ART

It is frequently of great utility to prepare a compound including a chemically active agent wherein the agent is masked or prevented from reaction with the environment for a specified or predictable time factor under known conditions. In addition, under certain circumstances, it may be highly desirable to have a system that permits a continuous controlled release of an agent maintaining an optimum level of the agent in the respective environment for its therapeutic or otherwise beneficial effect. Examples of these types of utilizations include encapsulation of drugs, blockage of active sites on chemical moieties during organic synthetic reactions and delayed release of agents. Examples of well known delayed release of agents are controlled release cold medicines, and the like, which are adapted to dissolve at varying rates within the body such that predictable amounts of the medicine are dispensed into the bloodstream over an extended time period. Most "twelve hour" cold medicines utilize this type of approach.

One of the most common methods of achieving a predictable controlled release mechanism of an active chemical agent is to encapsulate the agent with another material which gradually degrades in the desired medium. The encapsulating material physically surrounds the active agent in such a manner that the agent is not released into the bloodstream, or other environment, until the encapsulating material has been eroded or degraded by the passage of time and contact with the environment. One example of this might be in the coating of a drop of active agent with an encapsulating layer of oil which is only marginally soluble in an aqueous-based environment. The passage of time and exposure to the environment gradually erodes the coating of encapsulating oil until in the mechanism of diffusion coupled with direct physical dissolution, the active agent is released into the environment. The active agent can then react in a controlled manner in its respective environment to produce its desired effect.

A similar method is to trap molecules of the active agent within a surrounding polymer matrix. The matrix structure is such that exposure to an environmental material, usually water, causes the matrix structure to gradually degrade until the surrounding matrix structure is decomposed to the extent that the active agent molecule is permitted to escape into the environment. An example of a method of providing such matrix capture of active material is shown and described in U.S. Pat. No. 4,304,767, issued to Heller, et al. The Heller, et al. patent utilizes a polymer structure based upon ketene acetals reacted with polyols to provide an encasing polymer matrix for biologically active materials. The bonding structure of the ketene acetals and polyols, an orthoester, is subject to hydrolysis, that is, it is subject to degradation in a gradual manner upon contact with water. The restriction of the active material in the Heller, et al. invention is accomplished primarily by physical spatial enclosure, although under certain specified conditions where the encapsulating matrix is to be generated in the neat phase with the active agent in situ, it is possible to encounter a degree of cross-linking with the active agent.

The usefulness of structures such as that taught in the Heller, et al. patent is significantly dependent upon the unique bioerodable, or hydrolyzable, bonding structure which results from the reaction between hydroxy-containing monomers, namely polyols, and ketene acetals. This area has not been widely explored due to the prior difficulties in preparation, storage and handling of the necessary ketene moieties. To a certain degree, this difficulty has been alleviated by the teaching of U.S. Pat. No. 4,532,335, issued to Helwing. The Helwing patent discloses methods for preparation of substituted ketene acetals.

The ketene acetals, analogous vinyl ethers, and thio-analogs of these, are believed to undergo condensation reactions under acidic conditions with various functional groups via a carbonium ion mechanism. The bonds so formed between the ketene acetals or vinyl ethers and hydroxyl groups are readily hydrolyzed under even mildly acidic conditions. It is postulated that similar results will be obtained between various other functional groups on active agents and ketene acetals or vinyl ethers, and that these linkages will be hydrolyzable with degradation of the covalent bond in the presence of water providing an ideal mechanism for controlled release of chemical or biological agents.

In order to best achieve the desired rate of controlled release of the intended active agent, it is important to have control in design of the structural composition, namely its hydrophobicity, which will most effect the release rate via hydrolysis. In prior art structures this was primarily accomplished by varying the thickness of the encapsulating material, and, to a lesser extent, by chemically structuring the encapsulating matrix material to have a greater or lesser degree of hydrophobicity. In the present invention, as active agents will be bonded directly to the controlled release matrix, specific structural design of the base component system will most directly affect control over the hydrophobicity of the overall matrix. Improvements in the methods of adjusting controlled release of the active agent are always desirable.

One common disadvantage of prior art methods of providing timed released of active agents is that the ratio of inert (non-active) material to that of the active agent is typically very high. In the case of encapsulating materials it is necessary to provide a quantity of encapsulating inert material sufficient to totally spatially enclose the active agent and to protect it from premature release. In the case of matrix-based agent encapsulation, the matrix is typically a much higher percentage of the overall molecular weight of the structure than is the active agent. This can lead to cumbersome spatial situations and can increase the cost of manufacture of the overall product. For example, in Heller, et al., an example is given which shows a ratio of 4:1 matrix to agent. The present invention will allow for ratios of "encapsulating matrix" (i.e., base component) to active agent well below 1:1 depending on the molecular weight of the base component versus that of the active agent. The quantity of inert material necessary to properly mask the active agent may also lead to problems with solubility and transportability. For example, matrix-encased active agents such as those described in Heller, et al. may be incapable of being utilized in intravenous injection techniques since the structure is so large that it would block blood carrying capillaries. This limits the usefulness of the technique.

Other difficulties common to prior art methods include restrictions on available agents due to relatively high fabrication temperatures; limited modes of delivery and limitations in modifying the hydrophobicity of the resulting structure. Structures formed in prior art methods with polymeric encapsulation cannot effectively utilize easily thermally degradable active agents since the encapulating fabrication process requires elevated temperatures. The bulky polymeric structures of the prior art are also difficult to utilize in delivery schemes such as intravenous injection and spraying over surfaces, such as leaves. Furthermore, adjustments in the hydrophobicity of polymeric encapsulation matrices are complex and cumbersome to accomplish. All of these limit the usage and/or add to the cost of producing and delivering the controlled release structures.

None of the prior art techniques and compounds have been entirely successful in providing readily predictable timed or controlled release of active agents to an environment in an economical and efficient manner. All have suffered from disadvantages such as cumbersome structure, excess of inert material, difficulty of manufacture, high cost of materials and other problems.

BRIEF DESCRIPTION OF THE INVENTION

It is an object of the present invention to provide an aggregation of useful chemical compounds wherein a chemically active agent via its polar active (PA) functional group is covalently bonded with a carbonium ion mechanism ("CIM") base group, the bond therebetween being hydrolyzable in a predictable manner, resulting in controlled release.

It is another object of the present invention to provide combinations of active agents with CIM groups in both a capped manner and a leashed manner.

It is a further object of the present invention to provide a structure whereby active agents may be masked by covalent bonds rather than physical structural blocking.

It is yet another object of the invention to provide a direct one-to-one correspondence of base component to active agent reactive functional group.

It is still another object of the invention to provide a method of creating controlled release compositions at temperatures which do not degrade the active agents involved.

It is a further object to provide a wide choice of available usages for the compositions of the present invention by providing structures amenable to a wide range of modes of delivery.

It is still another object of the invention to provide enhanced control over the precise release rate in a specified environment by structurally modifying the composition components, thereby altering the hydrophobicity of the resulting composition.

The present invention is an aggregation of compositions consisting of a hydrolyzable covalent bond formed between a base structure and an active agent structure. The base components utilized are commonly describable as organic moieties capable of forming covalent bonds via a carbonium ion mechanism. These moieties are not known by any common generic term but are referred to herein as "CIM" groups. The active agent structures are selected from groups of organic moieties including polar active groups with CIM-reactive bonding sites. These moieties are also not describable in any commonly recognized manner but are referred to herein as "PA" groups. The combinations are particularly adapted for use in controlled release of the active agents by way of hydrolysis. The usefulness of the combinations of the present invention is found in a wide degree of chemical and biological applications including drugs, insecticides, herbicides, organic synthesis and customized timed or controlled release chemistry.

Briefly, the preferred embodiments of the present invention are novel compositions of matter formed by covalently bonding an active agent having a functional polar active (PA) group to a base component substrate including one or more CIM base component groups capable of reacting in a carbonium ion mechanism to form an orthoester or orthoester-like linkage. The inventive compositions of matter have the common property that the covalent bond joining the active agent to the base component is predictably hydrolyzable. The preferred base components include CIM groups selected from ketene acetals, vinyl ethers, ketene thioacetals and vinyl thioethers. The base components may either be in monomer form, or in a multiple CIM-group base component configuration that is either non-polymeric or may be placed on a polymeric backbone. The preferred active agents contain PA groups in the nature of organic functional sub-groups including those from alcohols, phenols, carboxylic acids, thiols, amines, phosphate esters, sulfonic acids, oximes, amides, and urethanes.

A group closely related to the alcohols is the cyanohydrin group and it is predicted that its behavior in reacting with the CIM groups on the base component will be analogous to that of the alcohols. Similarly, hydrazones and phenylhydrazones are also predicted to behave in a like manner to the amine family of PA groups. Also, semicarbazones are anticipated to behave similar to the amide family of PA groups. In addition, metallic and non-metallic core atoms, such as boron, arsenic, bismuth, mercury, copper, zinc and so forth, having both an alkyl group or groups attached to themselves in combination with a hydroxyl group or groups are considered to be suitably reactive with the CIM groups in the present invention to yield orthoester-type linkages in a manner similar to that ranging from the alcohols through the phosphate esters on up to the sulfonic acids in levels of acidity and reactivity towards the CIM groups.

The type of linkage existing between the base component and the active agent is an orthoester link in the case of ketene acetals as the CIM group combined with either alcohols or phenols as the active agent, and in the hydrolytic nature of an orthoester-like linkage with alternate CIM groups and PA groups. In the case of vinyl ethers as the CIM group combined with either alcohols or phenols as the active agent, the linkage is either an acetal or a ketal, and in the hydrolytic nature of an acetal-type or ketal-type linkage with alternate PA groups or the thioether variation; for the purposes of this invention in order to simplify the terminology used, due to the similar hydrolytic mechanism involved, linkages between any of the CIM groups combined with any of the PA groups will be referred to in general as orthoester-type linkages. The linkages of each of the combinations have common properties of being hydrolyzable in a predictable manner.

The preferred method of forming the novel compositions of matter is to prepare the base component, including at least one CIM group, either in a monomeric form, or multiple CIM group form, or in a polymer backbone form and then to bond the active agent at the molecular level, including at least one PA group, thereto in a ratio of one-to-one of active agent PA group to base component moiety. The process is controlled to obtain complete covalent bonding and to avoid cross-linking and structural enclosure of the active agent by the base component, particularly in the case of non-polymeric multiple CIM group systems or in leashed systems. Only mono-PA group agents are intended to be incorporated into a leashed (or non-polymeric multiple CIM group) system in order to avoid undesirable cross-linking, which can lead to unpredictable structures and prevent certain modes of controlled release delivery. With the base components and active agents of the preferred embodiment, the process may be undertaken at relatively low temperatures to avoid thermal degradation during incorporation of the active agents into the ultimate composition.

In certain cases it is preferred that the ketene acetal or vinyl ether concentration be tempered to a lower level by incorporating non-ketene acetal or non-vinyl ether type groups, particularly on the leashed systems; i.e., using either saturated or unsaturated acetals or ether groups which will not undergo rearrangement to either ketene acetals or vinyl ethers, respectively, in conjunction with the CIM forming base groups. Further, such non-CIM groups can be used to contribute to the overall hydrophobicity level. In addition, the unsaturated non-CIM type acetals or ethers can be used for free radical crosslinking where desired. The use of non-CIM forming acetals or ethers, particularly in the leashed systems, can help promote more complete reaction of the CIM base groups with especially large active agent moieties which can be inhibited otherwise by steric hindrance.

An advantage of the present invention is that new compositions of matter may be created which are subject to predictable hydrolysis under selected environmental conditions.

Another advantage of the present invention is that the preparation of the inventive composition may be undertaken at low temperatures thereby permitting incorporation of temperature sensitive agents into the controlled-release matrix.

A further advantage of the present invention is that the inventive compounds may be formed in either a capped or leashed manner.

Another advantage of the present invention is that the compositions may be formed with varying degrees of hydrophobicity imparting excellent control over release and residence time in the applied environment.

An additional advantage of the present invention is that low molecular weight active agents will be covalently bound up within the controlled release matrix in such a manner that undesirable plasticization of the release matrix will be prevented, particularly in the leashed polymeric systems.

A further advantage of the present invention is that the compositions may be custom tailored for applications in medicinal, veterinarial, chemical, botanical and insecticidal usages.

Still another advantage of the present invention is that the combination materials themselves may have specific novel chemical or biological effects independent of those of the unaltered active agent.

Yet another advantage of the present invention is that the compositions, particularly in the capped form, or when leashed to low molecular weight base component systems or polymers, may be created having a relatively low molecular weight and compact stoichiometry with respect to prior art timed release compositions which would permit, e.g., such applications as direct injection into the bloodstream, or, e.g., applications of evenly dispensed films such as sunscreens on the skin or long-term insecticides or fungicides sprayed onto plants.

An additional advantage of the present invention is foreseen in reduced toxicological ramifications, particularly in the case of agents bound up in the leashed form, by limiting unwanted absorption to both the operator applying such an agent and to, for example, a plant being sprayed with the leashed agent preventing unwanted absorption of the agent itself by the plant. Capping of agents may similarly contribute to reducing the toxicity, but to a lesser degree. Furthermore, the base component can be designed to minimize its possible toxic contribution to an innocuous level; a vital consideration for medical applications.

Another advantage of the present invention is that compounds may be created with much lower matrix to active agent ratios than those of prior art controlled release materials.

A still further advantage of the present invention is that the ketene acetal and thioacetal compositions may be utilized in organic synthesis in the combined form to permit modification of portions of the active agent other than the PA group, with the CIM base component acting as a blocking group to prevent unwanted chemical activity on the linked PA group of the active agent.

These and other objects and advantages of the present invention will become clear to those skilled in the art in view of the description of the best presently known modes of carrying out the invention and the examples as set forth herein.

BEST MODE OF CARRYING OUT INVENTION

The primary embodiments of the present invention are an aggregation of compounds formed by covalently bonding any of a group of selected active agents via their PA groups to ketene acetals, vinyl ethers and similar CIM group-containing base components. The preferred compounds have the common property that the covalent orthoester-type bond joining the active agent to the base component is hydrolyzable in a predictable and adjustable manner. This permits the inventive compositions to be utilized for controlled or timed release delivery of chemically active or biologically active agents in specific environments. Among the principal uses of the compounds of the present invention are insecticides, drugs, herbicides and chemical synthetic blocking agents.

The present invention also includes an inventive method of forming and manufacturing the compositions. The methods of preparing these compositions are required in order to successfully utilize the compositions and to understand the mechanisms by which the hydrolyzability of the covalent bond may be adjusted.

Each of the compositions of the present invention has two distinct moieties joined by a hydrolyzable covalent bond. The two major components of the compositions are an active agent component and a base component. The active agent component is the chemical agent which is desired for a particular purpose, such as an insecticide, a drug or some other agent desired to accomplish a particular chemical or biological reaction. The active component will have this chemical or biological effect when it is in its free molecular form but will not have the same effect when it is restricted in the inventive composition by the covalent bond. The hydrolytic decomposition of the covalent bond will act to release the agent so that it may again act in its original molecular form. All of the active agents which are viable for incorporation into the inventive compositions have one or more polar active subgroups (referred to as "PA" groups) available for bonding.

The base component, acting as a vehicle of delivery for the active agent, is designed to be generally innocuous from a biological standpoint so that its presence in the body or environment after decomposition of the covalent bond does not create a toxicity problem or result in unwanted reactions. The base component must also be selected to form the appropriate hydrolyzable covalent bond with the active agent component, with the bond having the desired degree of hydrophobicity. All of the base components which are viable for incorporation into the inventive compositions have one or more carbonium ion mechanism subgroups (referred to as "CIM" groups) available for bonding, either in a monomeric form for capping, or in a polymeric form for leashing.

The base components that have been found to be preferred embodiments in the present invention are those which contain one or more CIM groups which are capable of reacting in a carbonium ion mechanism with the polar active groups (PA groups) on the selected agents. Two primary acceptable CIM groups are ketene acetals (which come in noncyclic and cyclic forms) and vinyl ethers (See Formulas C-1 and C-2 below). The sulfur substituted analogs of these components, namely ketene thioacetals and vinyl thioethers (See Formulas C-3 and C-4 below) are also considered to be appropriate. With respect to all of these base components, a high degree of substitution is allowable. Various "R" groups may be selected for substitution on the base components, provided that they do not lead to unwanted side reactions, namely that they are not independently reactive either in a self reactive manner within the base component molecule or with portions of the selected active agent during the intended principle reactions whereby the initial CIM-base components are generated and the subsequent CIM-base component/active agent matrix is formed. Selection of appropriate substitution groups on the base component may be accomplished to alter the hydrophobicity of the resulting composition and to consequently alter the residence time of the release matrix in the selected environment.

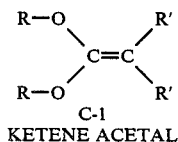
C-1
KETENE ACETAL

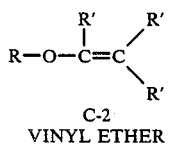
C-2
VINYL ETHER

-continued

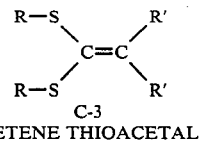
C-3
KETENE THIOACETAL

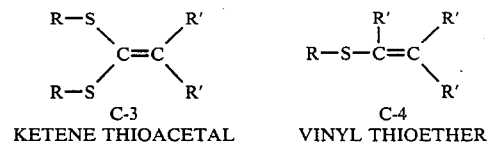
C-4
VINYL THIOETHER

The R and R' groups need not be identical amongst themselves or to each other. The formulation R⌒R indicates that the two R groups may be joined together to form a cyclic group or may be separate, unconnected groups.

Where R and R' are methyl or higher analogs, they may be drawn from the pool of possible groups including essentially hydrocarbon groups, primarily alkyl, aryl, cycloaliphatic or aralkyl groups, and may be saturated or unsaturated.

By "essentially hydrocarbon," it is meant that the groups R or R' may contain hereto atoms provided they do not inhibit the reaction required to prepare a controlled release matrix to an unacceptable degree, do not inhibit degradation of the release matrix to an unacceptable degree and do not give rise to toxic or difficulty metabolizable degradation products.

In addition to various R group substitutions on the CIM groups in monomeric form, it is also feasible to incorporate the base components in a polymeric backbone. This permits the creation of a polymeric composition yielding repetitive CIM base components, each acting independently as a viable moiety.

Polymeric support substrates for the leashed systems would include polyvinyl alcohol, dextran, cellulose and similar polyhydroxy polymers. Intermediate to a monomeric and a polymeric CIM base component system is a multiple functional CIM group system based on such substrates as pentaerythritol, inositol and other simple polyhydroxy compounds including sugars. For medical applications, either for humans or animals, where toxicity is a factor, use of 1,2 propylene glycol, pentaerythritol, inositol and like innocuous analogs should present no problem; however, most glycols would not be acceptable unless their use was at a low enough level to avoid causing measurable toxic effects. For uses outside of medicine, these considerations are less critical. Vinyl ether base component analog could employ monohydroxy alcohols or phenols as part of their base component system, in addition to the aforementioned substrates above.

A partial list of viable PA groups to be used as portions of acceptable active agents, particularly those of expected commercial importance, are set forth below in Table 1. The common thread found in the various active agents is that each include one or more functional PA subgroups which are capable of forming the desired hydrolyzable covalent bond with the CIM subgroup of the base component in a predictable manner. The primary functional PA subgroups which have been found to be, or are considered to be effective, include alcohols, phenols, carboxylic acids, thiols, amines, amides, urethanes, phosphate esters, sulfonic acids and oximes. In addition to these PA subgroups, the following are considered to also apply as previously discussed: cyanohydrins, hydrazones, phenylhydrazones, semicarbozones and active agents having metallic and/or non-metallic core atoms such as boron, arsenic, antimony, bismuth, mercury, copper, zinc and so on, having both as alkyl group or groups attached to themselves in combination with a hydroxyl group or groups. Various other functional PA subgroups may also be found to be viable but those named above are those which are presently believed to be effective. Formulae for these are shown below as PA-1 through PA-10.

TABLE 1

| Designation | Description | Functional Group Structures |
|---|---|---|
| PA 1 | Alcohols 1°, 2°, 3° | R—OH |
| PA 2 | Phenols | (phenol ring with R substituents and OH) |
| PA 3 | Carboxylic acids | R—COOH |
| PA 4 | Thiols, 1°, 2°, 3°, aromatic | R—SH |
| PA 5A | Primary amine | R—NH$_2$ |
| PA 5B | Secondary amine | (R)$_2$—NH |
| PA 6A | Monoalkyl phosphate ester | RO—PO—(OH)$_2$ |
| PA 6B | Dialkyl phosphate ester | (RO)$_2$—PO—OH |
| PA 7 | Sulfonic acid | R—SO$_3$H |
| PA 8 | Oxime | R=NOH |
| PA 9A | unsubstituted amide | R—CONH$_2$ |
| PA 9B | monosubstituted amide | R—CONHR |
| PA 10 | urethane | R—COONHR |

The hydrolyzable covalent bond between the active agent component and the base component will vary in nature to a certain degree depending upon the identity of the functional group of the PA agent component and the CIM base component. In the case of the non-sulfur containing ketene acetal CIM base group moieties and either an alcohol or a phenol as the PA functional group, the covalent bond structure is in the nature of an orthoester linkage. With respect to other active agent functional PA groups and CIM base components, the bond structure will not be a pure orthoester linkage but will be of a similar hydrolyzable nature. As an example of a similar hydrolyzable linkage is the case of a non-sulfur containing vinyl ether CIM base group moiety reacting with either an alcohol or a phenol PA group to yield a covalent bond that is either an acetal or a ketal depending on the substitution of groups on the vinyl ether carbon Cl. Precise nomenclature has not yet been established for the bonds of all the alternate compositions between the different CIM base group moieties and PA functional groups, but the central covalent bonds formed in all of the inventive compositions will be generally referred to herein as "orthoester-type" linkages.

Inventive compositions of the present invention may be formed in either monomeric or polymeric modes. In the case of reaction between unimolecular base components having a single base component functional CIM group formed thereon, and active agents which are monofunctional or polyfunctional in nature with respect to the stoichiometry of the reaction, the resulting composition will be a complete entity in itself comprising a single active agent molecule and as many CIM base groups as required to react with the available PA groups on the active agent molecule. This type of one-to-one bonding is referred to herein as "capping." In the event that the base component is formed on a polymeric backbone with the active agent component indirectly tethered to the polymeric backbone through the orthoester-type linkage, the nature of the resulting composition is referred to as being "leashed." In the case of the "leashed" systems, composition is restricted to only monofunctional PA group active agents reacting with the polymeric, polyfunctional CIM base component substrate in order to avoid unwanted cross-linking, which would result in technical problems in preparing the controlled release systems as well as limiting the modes of delivery.

As an intermediate system that is in between the defined "capped" or "leashed" matrices just described is the case where the CIM base component is based on a substrate that permits the formation of two or more CIM subgroups, yet is not polymeric in itself. This system is also restricted to mono-PA functional active agents to avoid unwanted cross-linking. An exception to this exists where the CIM substrate contains two CIM subgroups and the active agent has two PA groups; in this case it is permissible to proceed with this reaction since it will not lead to cross-linking.

The generic formation mechanism of the compositions of the present invention is shown below in equation EQ-1. This equation shows the CIM group (I), with a ketene acetal as an example in this case, having a carbon-carbon double bond which is subject to conversion to a carbonium ion structure (II) in the presence of an acidic catalyst. For a ketene acetal or ketene thioacetal the Z groups will be in the nature of OR or SR, respectively. The same mechanism applies to the corresponding vinyl ethers and vinyl thioethers and is shown in EQ-1A.

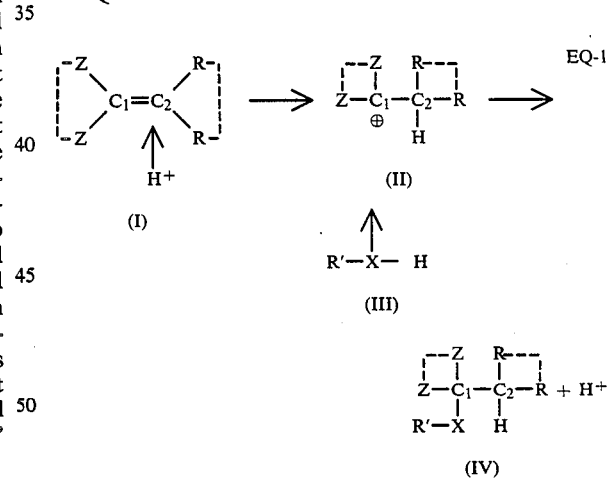

where Z=—OR or —SR; HX=PA group

-continued

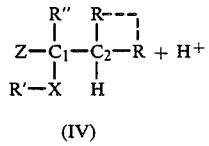

(IV)

where Z=—OR or —SR; HX=PA group; R" may be —H, —CH$_3$ or higher analog.

The active agent is generically represented as R'XH (III) with XH being a PA group as shown above. The PA groups each include an available hydrogen capable of being separated from the X component of the PA functional group during the reaction.

The reaction mechanism involves first forming the carbonium ion moiety (II) by activating the base component CIM group with the aid of an acid catalyst, either a Lewis or Bronsted acid catalyst, or even iodine in pyridine (charge-transfer complex). Heller, et al. suggests a suitable variety of catalyst and solvent candidates. The carbonium ion moiety (II) then reacts with the XH portion of the active agent (III) to form the generic inventive composition (IV). The orthoester-type linkage formed is believed to propagate the reaction by releasing the available hydrogen from the PA group as a proton to activate another CIM moiety. The summation of this mechanism is that the catalyst proton ends up on carbon atom C2 with the active agent linked via its X functional group to carbon atom C$_1$.

The orthoester-type linkage which is formed during the course of the reaction in EQ-1 and EQ-1A is stable at normal environmental temperatures, so long as no water is present in the environment. However, in the presence of water, the orthoester-type linkage is subject to hydrolysis as shown in equation EQ-2 with the Z group representing either the ketene acetal or thioacetal. EQ-2A shows the analogous mechanism for the vinyl ethers and thioethers. The higher the acidity of the environment, and therefore the greater the H$_3$O$^+$ concentration, the more rapid the rate of hydrolysis. The degree and rate of hydrolysis are also dependent on the hydrophobicity of the composition, which may be primarily adjusted by selecting the appropriate substitution groups for the base component.

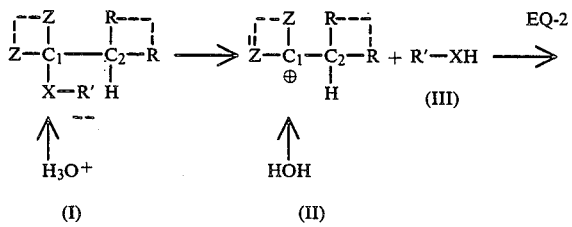

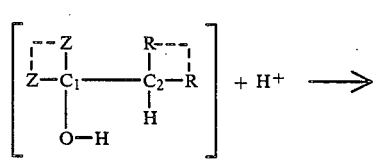

UNSTABLE

-continued

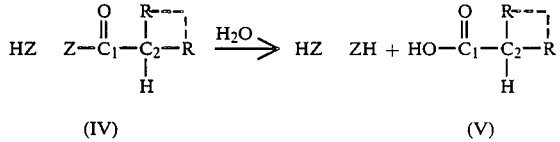

(IV)         (V)

where Z=—OR or —SR

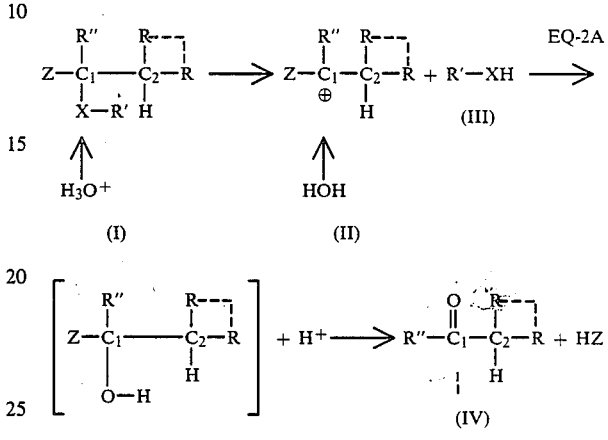

where
Z=—OR or —SR
R"=H; (IV) is an aldehyde
R"=CH$_3$ or higher analog; IV is a ketene The reaction of EQ-2 also involves a carbonium ion mechanism. The same mechanism applies to the corresponding vinyl ethers and vinyl thioethers. However, in this reaction C$_2$ is fully substituted and is not available for reestablishment of the double bond. Therefore, after the original active agent R'XH has been freed by the hydrolysis reaction, an OH group takes its place on C$_1$. This arrangement has limited stability and rapidly decays into a simple ester which will continue to hydrolyze further, eventually liberating a carboxylic acid and an alcohol or other hydroxy supporting substrate. The final degradation products for the analogous vinyl ether base component system will be release of the hydroxy-supporting base component substrate and either an aldehyde or a ketone, depending on the substitution on carbon C$_1$, in the original vinyl ether group.

The hydrophobicity of the inventive compositions may be altered such that the composition hydrolyzes at different rates. This may be accomplished by varying the composition of the various R groups on the base component and on the active agent. Ordinarily the active agent is fixed for a given application due to its particular chemical properties so hydrophobicity control is accomplished primarily by substitutions on the base component. Generally, it may be stated that hydrophobicity increases with the molecular weight of both aliphatic and aromatic subgroups with the aromatic groups believed to generally result in greater hydrophobicity than aliphatic groups. This is true whether the base component is in monomeric form or in polymeric form. In its polymeric form, the hydrophobicity of the completed matrix may be increased just by the sheer molecular weight and size of a more massive polymer backbone.

If a particular desired active agent has a high molecular weight such that a high degree of hydrophobicity will be inherent in the composition, then it may be desirable to utilize a low molecular weight base component to increase the rate of hydrolysis. Modification of the composition components may be accomplished as desired for the particular agent and intended use.

In general terms, to prepare the ketene acetal, the beta-unsaturated acetal is either commercially obtained or is generated readily from the starting alpha-unsaturated aldehyde by reacting it with an orthoester using a trace amount of acid catalyst. Some suggested precursors are acrolein, methacrolein and crotonaldehyde. This is followed, if desired, by a transacetalization step in which monohydric alcohols as part of the initial acetal may be substituted by higher monohydric homologs or analogs, or by dihydroxy compounds such as various glycols, or by polyhydric compounds in various low molecular weight compounds, sugars for example, or by polyhydric polymers. Following transacetalization, for polyhydric systems containing three or more hydroxyl groups, it is then desirable to cap any residual free hydroxyl groups by preferably etherification, or by other hydroxyl capping reactions stable to the subsequent reactions. Alternate capping reactions may include those using an isocyanate to generate a urethane cap, a vinyl ether to generate an acetal or ketal cap, or even the use of an ester. Following capping of residual free hydroxyl groups, the beta-unsaturated acetal is rearranged by the method of Helwing into the alpha-unsaturated acetal state, otherwise known as a ketene acetal. Alternate solvents to those detailed in the Helwing reference may include amines in general such as hexamethylenediamine, piperidine, piperazine, pyrrole and pyrrolidine. These may be used by themselves or in various ratios to each other to obtain the best yielding reaction solvent. Some suggested co-solvents for use with those just mentioned above may include pyridine, triethylamine, tributylamine, ethers including the glymes, morpholine and symdimethylethylenediamine. The ketene acetal base component system can then be reacted with the polar active groups on the active agent under the appropriate acidic conditions. A similar approach to that described above is used to generate the thioacetal analog.

In a similar vein, the vinyl ether counterpart to the ketene acetal-based system is likewise generated. A starting alpha-unsaturated alcohol can be etherified onto any of several hydroxyl-containing candidates ranging from simple monohydric alcohols or phenols, to 1,2 and 1,3 glycols or other low molecular weight di- and higher polyhydroxy compounds and continuing on up to polymeric polyhydroxy systems, such as poly (vinyl alcohol).

Three suggested routes for the preparation of vinyl ether-based CIM base component systems are presented below. The first method consists of generating, for example, the diallyl sulfate ester of allyl alcohol which can then be used to etherify any hydroxyl or phenoxy group in an analogous fashion to that of using dimethyl sulfate to etherify hydroxyl compounds using aqueous sodium hydroxide. To insure that all the hydroxyl groups are capped, or blocked, particularly in the case of a polymer such as poly (vinyl alcohol), the reaction can be driven to completion or dimethyl sulfate used to more vigorously cap residual free hydroxyl groups. The etherified substrate is then isolated and ready for the rearrangment step.

In an alternate method, the hydroxy substrate is treated with either sodium or potassium, or in a strongly basic medium consisting of sodium amide, or sodium or potassium hydride in an ether or amine solvent to generate the necessary alkali metal alkoxide which is then treated with the desired alpha-unsaturated alkyl or aryl-substituted alkyl halide, such as allyl or crotyl chloride, to yield the beta-unsaturated ether precursor. The precursor is isolated and prepared for the rearrangement step.

Yet another method uses a reverse approach to the outlined process immediately above where the starting substrate for the CIM base component is an alkyl or aryl-substituted alkyl halide spanning the gamut from monomeric alkyl halides on up to polymeric-based systems including such examples as poly (vinyl chloride) and poly (epichlorohydrin). The halide substrate is then treated in an ether or strongly basic amine solvent with the sodium or potassium alkoxide of the desired alpha-unsaturated alcohol; for example, allyl or crotyl alcohol. If some residual free chloride groups remain, these may be treated to a more vigorous attack by either sodium or potassium methoxide, ethoxide or tert-butoxide. Alternately, the residual halide groups may be left alone if they are acceptable in the degradation product. The etherified precursor substrate is then isolated and prepared for rearrangement of the beta-unsaturated ether to the alpha-unsaturated form, otherwise known as a vinyl ether.

Once the beta-unsaturated ether precursor has been prepared, it may be readily rearranged into the vinyl ether form using either the method of Helwing, employed to rearrange unsaturated acetals into ketene acetals, or a closely allied variation thereof employing a strong base, such as potassium tert-butoxide, in either an amine-type solvent or an aprotic solvent, such as dimethyl sulfoxide. The product vinyl ether base component so formed is then ready to be reacted with the active agent PA groups to yield either an acetal-type or ketal-type covalent linkage depending on whether the alpha-vinyl ether carbon has only a hydrogen atom attached to it, or is substituted, either with a methyl group or higher alkyl or aralkyl group, respectively. In the case of a vinyl ether CIM group reacting with either an alcohol or a phenol, the resulting bond formed is actually an acetal or ketal defined by the conditions above. For the sake of simplicity in this invention description, covalent bonds so formed between vinyl ether CIM groups and active agent PA groups will also be generically referred to as orthoester-type linkages, regardless of whether they are true acetal or ketal linkages, or acetal-type or ketal-type linkages.

The prepared vinyl ether CIM base component can then be reacted with the active agent in an analagous manner as described for the ketene acetal-based CIM base component system, both in the earlier discussion on ketene acetals above and in Examples 3 and 4 below. The thioether analogs are expected to behave in a like manner to the vinyl ethers.

The inventive process of forming the unique compositions and the precise structure of the compositions is best understood in terms of specific examples. Since the initial step in creation of the composition involves creation of the base component, this step will be illustrated first as Example 1. This example shows the formation of a typical monomeric ketene acetal base component of the type shown in Formula C-1 above from building blocks of a diethyl acetal and a diol.

EXAMPLE 1

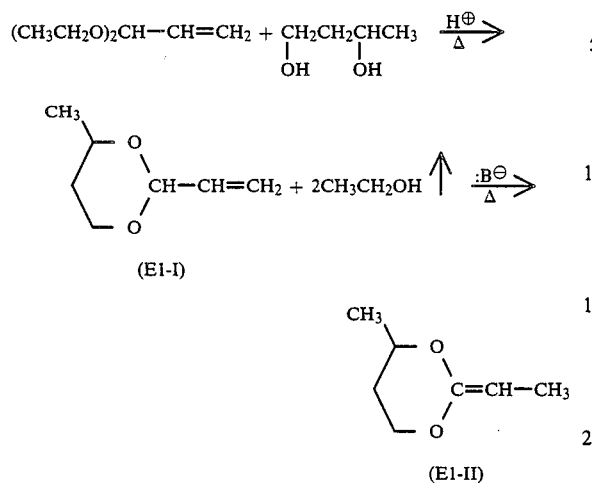

(E1-I)

(E1-II)

Into a 250 ml round-bottomed flask, outfitted with a distillation head, a condenser and a receiving flask, is added 130.19 grams (1.000 mole) of Acrolein diethyl acetal (should the initial starting acetal not be conveniently available, it may readily be prepared by taking the appropriate unsaturated aldehyde and acetalizing it using, for example, triethyl orthoformate with only a trace amount of acid catalyst to initiate the reaction) plus 90.12 grams (1.000 mole) of 1,3-Butanediol and 0.50 grams (0.0026 moles) of p-TSA (p-Toluenesulfonic acid monohydrate) as catalyst. The procedure is conducted under a blanket of anhydrous nitrogen gas. The transacetalization mixture is gradually heated up to 120° C. to drive the reaction towards the cyclized acetal by constant removal of the liberated ethanol. When the reaction has reached a level of practical completion, the mixture is cooled, neutralized with TEA (triethylamine), extracted in an ether/water phase, dried over anhydrous potassium carbonate, the ether evaporated and the product adequately purified by distillation. The isolated product, Compound $E1^{-I}$, is then rearranged by placing 48.15 grams (0.429 moles) of potassium tert-butoxide into a 3-necked, 250 ml round-bottomed flask under a blanket of dry nitrogen, adding 100 ml of anhydrous ethyledediamine, allowing the mixture to dissolve, and then adding 50.00 grams (0.390 moles) of Compound E1-I. The reaction set up is outfitted with a reflux condenser, the reaction mixture maintained under nitrogen and heated up to 100° C. and held there for 24 hours. The reaction mixture is then poured into a liter of water and extracted with pentane to draw out the ketene acetal. The pentane extract is dried over anhydrous potassium carbonate, the pentane then stripped off by rotary vacuum evaporation and the concentrated product purified by distillation through a spinning band column. A good yield of the product ketene acetal is expected.

The base component may also be formed in a polymeric mode rather than the monomeric mode shown in Example 1. The polymeric backbone adds molecular weight, stability, and hydrophobicity and is especially useful in situations where it is desired to increase the residence time for controlled release and also reduce migration from the site of application. One method of forming a polymeric base component is illustrated below as Example 2.

EXAMPLE 2

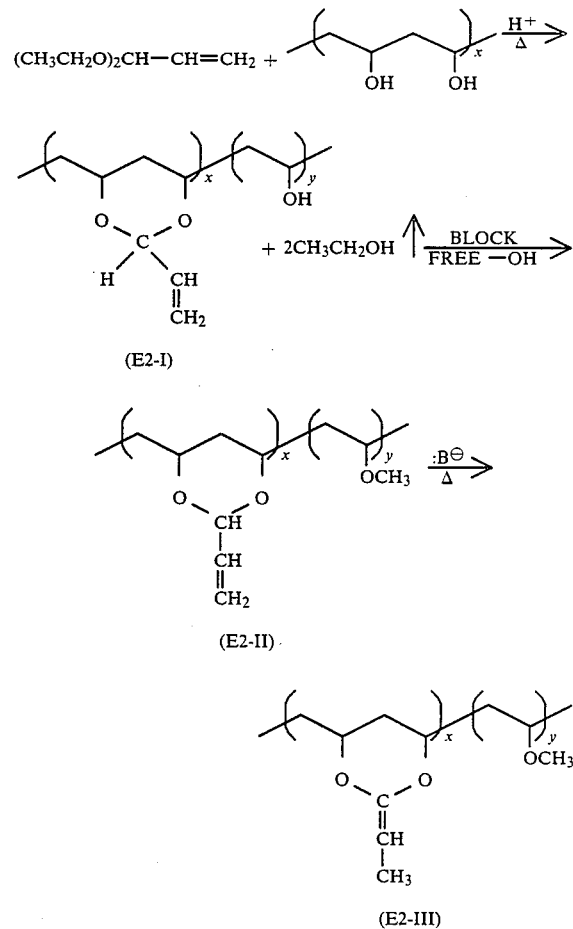

(E2-I)

(E2-II)

(E2-III)

Into a 3-necked 500 ml round-bottomed flask, outfitted with a distillation head, condenser and a receiving flask, is added 100 ml of anhydrous diglyme, 143.20 grams (1.100 mole) of Acrolein diethyl acetal plus 88.10 grams (1.000 mole-equivalent [2 hydroxyl groups: acetal group] of PVA* (Polyvinyl alcohol; *PVA spec: 86K MW, 100% hydrolyzed) and 0.50 grams (0.0026 moles) of p-TSA as transacetalization catalyst, all while under a protective cover of dry nitrogen. The mixture is gradually heated in steps from 100° to 150° C. and held there until the liberated ethanol can no longer be driven off. The mixture is allowed to cool to room temperature, the acid catalyst neutralized with TEA and the reaction mixture added dropwise to 2 liters of hexane containing 2 ml of TEA to maintain a basic environment. The precipitated poly-acetal polymer backbone can then be easily isolated by filtration, washed with 2–100 ml portions of fresh hexane and then dried under vacuum. To 50 grams of Compound (E2-I) in a 1000 ml 3-necked round-bottomed flask equipped with a reflux condenser is added 200 ml diglyme to dissolve the polymer. This is followed by 85 grams of aqueous sodium hydroxide containing 35.20 grams (0.880 moles) of sodium hydroxide. The mixture is maintained under rapid stirring and its temperature brought up to 50° C. using a water bath. An addition funnel is added containing 50.45 grams (0.400 moles) dimethyl sulfate which is added dropwise to the agitated mixture over a 30 minute period. Following addition of the dimethyl sulfate, the reaction temperature is increased to 75° C. and held there for an hour. The contents are then cooled and added dropwise to 1 liter of 2N ammonium hydroxide, the polymer recovered then dissolved in 100 ml THF containing 1 ml TEA, anhydrous potassium carbonate added to remove residual moisture and then filtered off, the remaining solution is then added dropwise to 2 liters of hexane containing 2 ml TEA, the precipitate washed with 2-100 ml portions of hexane/TEA and the recovered polymer, Compound (E2-II), vacuum dried. Into a 250 ml 3-necked round-bottomed flask equipped with a reflux condenser and under protection of dry nitrogen is placed 25.00 grams (0.198 mole-equivalents) of compound (E2-II) to which is then added 50 ml anhydrous diglyme, the polymer then being dissolved using magnetic stirring. In a 250 ml single-neck round-bottomed flask is placed 24.46 grams (0.218 moles) potassium tert-butoxide to which is added 100 ml of anhydrous ethylenediamine, the butoxide dissolved and the base solution transferred into the flask containing Compound (E2-II) via a stainless steel u-tube using nitrogen pressure. The mixture is heated to 100° C. for 24 hours, then allowed to cool to room temperature and is then dumped into a liter of water. To 20 grams of precipitate is added a solvent mixture such as 50 ml THF (tetrahydrofuran) containing 0.5 ml TEA, the precipitate dissolved, the solution dried over anhydrous potassium carbonate and then added dropwise to a non-solvent such as a liter of hexane containing 0.5 ml of TEA to protect the ketene acetal groups. The resultant precipitate is washed with 2-100 ml portions of additional hexane/TEA and then vacuum dried. A good yield of the product ketene acetal is expected. Compound (E2-III) must be carefully handled under anhydrous conditions to protect the ketene acetal groups (a dry box, or equivalent, is the best environment for such handling).

Once the base component has been formed as shown in Examples 1 and 2 it is ready for addition of the active agent component. The process of adding the active agent component is described below in Examples 3 and 4. The active agent selected for Example 3, namely, 5 - Androstene - 3β, 16α-diol was selected because of its exemplification of an agent with multiple PA groups. This compound (E3-I) has two available hydroxyl groups, both of which are effectively capped by the ketene acetal formed in Example 1 (E1-II). The resulting composition (E3-II) shows how multiple active sites may be capped on an active agent component. Example 4 shows an active agent being leashed to a polymeric form base component.

EXAMPLE 3

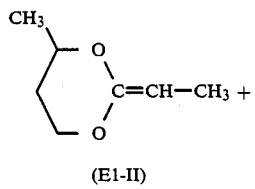

(E1-II)

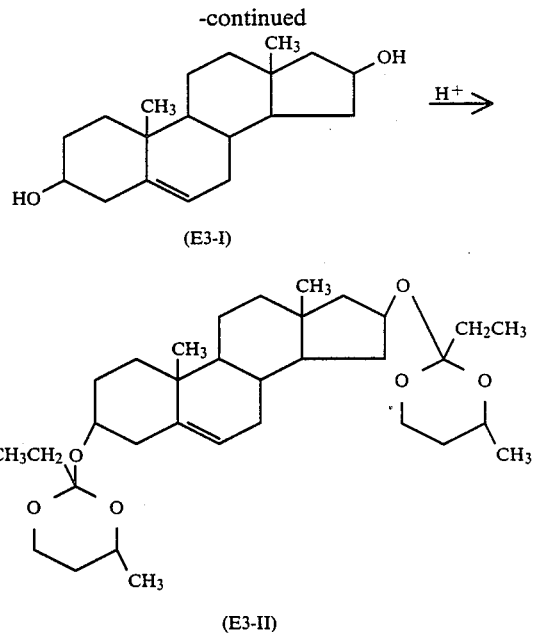

Into a 3-necked 250 ml round-bottomed flask equipped with a magnetic stirrer and a reflex condenser which is set up with a dry nitrogen purge with bubbler pressure relief is placed 20.00 grams (0.069 moles) of 5-Audrostene-3β16α-diol, Compound (E3-I). Through a septum via a syringe is then added 100 ml anhydrous THF and the diol dissolved. This is followed by 26.50 grams (0.270 moles) of Compound E1-II as created in Example 1, added via syringe and also allowed to dissolve completely. To the reaction mixture is then added 1.00 ml of $1 \times 10_{-4}$ mole of p-TSA per ml of THF as catalyst with the reaction mixture immersed in an ice bath to control the exothermic reaction. After 15 minutes, the bath may be removed and the mixture allowed to react further for an additional 45 minutes. The reaction may then be halted by adding 1.00 ml TEA. The product may be isolated by rotary vacuum evaporation concentrating the product and followed by recrystallization in an appropriate solvent system employing 1.00 ml TEA per liter of the solvent; the solvent should be anhydrous, preferably an ether or other non-reactive solvent, and maintained under anhydrous conditions while working up the product. A good yield of the product matrix as the capped agent, compound (E3-II), is expected. This composition has both hydroxyl groups capped by the monomeric base component.

EXAMPLE 4

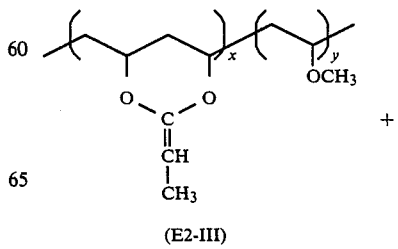

(E2-III)

+

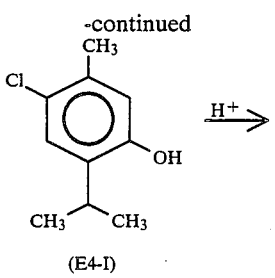

(E4-I)

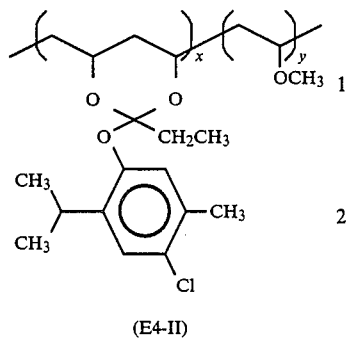

(E4-II)

Into a 3-necked 250 ml round-bottomed flask equipped with a reflux condenser and under a dry nitrogen purge is added 20.00 grams (0.159 theoretical mole-equivalents) of Compound (E2-III), as created in Example 2, followed by 100 ml of anhydrous THF. Using magnetic stirring the mixture is dissolved and then 43.91 (0.238 moles) of 6-Chlorothymol, Compound (E4-I), is added and dissolved followed by 1.00 ml of $1 \times 10_{-4}$ mole of p-TSA per ml of the THF catalyst solution. The exothermic reaction is allowed to run its course liberating its heat freely. After an hour, the reaction mixture is neutralized with 48.17 grams (0.476 moles) of TEA and the product recovered by adding the solution dropwise into 2 liters of hexane followed by filtration, two washings with hexane/TEA and vacuum drying under anhydrous conditions. A good yield of the product matrix, shown as Compound (E4-II), is expected and is a prime example of a leashed agent ready for controlled release usage.

The above stated examples are theoretical in nature in that the lack of appropriate laboratory facilities has made it impossible for the inventor to specifically test each of the examples. However, with the known properties of the compounds involved as set forth in the literature and including the inventor's prior experience with similar types of compounds and reactions, the inventor feels very confident in the predicted outcome described in the examples. The previously discussed patents to Heller, et al. and Helwing show to some extent similar type reactions to those illustrated in the examples cited.

As is clear from the above, the scope of possible compositions that can be created according to the present invention is extremely broad. A very wide number of base components may be created utilizing variously substituted CIM groups while a nearly infinite number of active agents, incorporating the requisite PA groups, may also be utilized. All of the inventive compositions are such that they may be created by the process of the present invention and all will be similar in that the CIM and PA groups will form a hydrolyzable covalent bond which will act to keep the inventive composition intact under environmental conditions until hydrolysis occurs.

Consequently, the above examples and illustrations are not intended to be limiting, but are instead to act as generic examples for preparing the full spectrum of possible compositions. Accordingly, the appended claims are to be interpreted as encompassing the entire spirit and scope of the invention.

INDUSTRIAL APPLICABILITY

The inventive chemical processes and the compositions created thereby of the present invention are expected to have extremely wide spread utility both in industry and in chemical research. Known uses for hydrolyzable covalent compositions such as those of the present invention, are to be found in the fields of medicine, veterinary medicine, agriculture, horticulture, entomology, and synthetic chemistry just to name a few areas.

Timed-release drugs for controlled introduction into the blood stream or other body tissues or cavities are well known, including compositions referred to as prodrugs. The inventive compositions are extremely well adapted for use in this field. Several areas and some specific examples of usage are already envisioned for the present invention. These include medicinal and veterinarial uses as prodrugs or even as entirely new drugs with modes of delivery such as intravenous, intramuscular or subcutaneous injection/implantation; intestinal transit; inhalation or transnasal administration; transdermal; topical use; dermal application; and other external uses. The form of the controlled release matrix for administration can span the gamut from neat solutions to solvent-based solutions to emulsions and even suspensions. Along these lines, the inventive systems could be used to deliver not only general drugs, but cancer drugs, hormones, vitamins, fungicides and even used as a more durable sunscreen. Outside of such medical applications, the inventive systems can be used as more effective insecticides and for such specific applications as a longterm control against termites, as an antimicrobial, mildicide, fungicide, herbicide, delivery of pheromones, insect repellant and even as a protective group in organic synthesis. Some of the methods of application for these commercial fields would include spraying, dipping and other modes of applying the controlled release matrix. Improvements over the prior art are provided by permitting a lower ratio of weight of inert material with respect to active material in the timed release matrix, in utilizing larger molecular weight active agents which may not be appropriate for physical, spatial enclosure of the type described in Heller, et al., also in low temperature fabrication permitting handling of temperature sensitive agents and in a broadening of the range in modes of delivery.

The preferred embodiment of the present invention may also be applied to a surface as a film of uniform consistency for use in several areas of application. As examples of this, one use for such films would be the spraying of plants to deposit an even, thin film of covalently linked insecticide; or as another example, to treat exposed and vulnerable areas of wood, particularly underneath a house or in the attic space with a sprayed-on application of a bound termiticide, such as pentachlorophenol. The chemically linked nature of the controlled release matrix affords not only the ability to apply such films, but permits the most compact physical structuring possible in a controlled release matrix as well as an assured even distribution of the desired agent.

Further, insects attacking such areas should be swiftly and efficiently overcome at the outset by the chemical release of the agent in the aqueous environment of their digestive tract.

Applications in the entomological, agricultural and horticultural areas would particularly relate to insecticides and herbicides which would have delayed release capabilities and reduced losses from evaporation, premature degradation of the agent, or from unwanted migration just by simply being washed off, thus reducing the frequency of application requirements. The inventive compositions may also, although this is not certain at this stage, have independent use as separate moieties where the combinations may have chemical properties which are independent of those of the components and may be usable in their own right, regardless of hydrolysis. Furthermore, the compositions based on ketene acetals may be valuable as blocking agents for chemical synthesis on other active agent groups wherein the PA groups are prevented from reacting during specific processes and may then be freed by hydrolysis for later reactions.

For all of the above reasons, it is believed that the inventive process and compositions will have widespread industrial and commercial utility.

I claim:

1. A composition of matter comprising:

an effective amount of a base component including at least one available CIM group; and an effective amount of an active agent component, wherein the active agent includes at least one available PA group and is attached by a covalent bond between said PA group and said CIM group in a non-crosslinked manner, wherein a CIM group is a moiety capable of forming a covalent bond by a carbonium ion mechanism with hydrogen releasing polar groups and a PA group is a hydrogen releasing polar group capable of forming a covalent bond with a CIM group, by way of an orthoester-type linkage.

2. The composition of claim 1 wherein said covalent bond is predictably degradable via hydrolysis such that the active agent component may be released in a controlled release manner under selected environmental conditions.

3. The composition of claim 1 wherein each PA group is selected from the aggregation comprising; alcohols, phenols, carboxylic acids, thiols, amines, amines, urethanes, phosphate esters, sulfonic acids, cyanohydrins, hydrazones and oximes, each said PA group being covalently bonded to a respective one of said CIM groups.

4. The composition of claim 1 wherein the base component is in monomeric form, includes a single one of said CIM subgroups and the active agent is capped thereto.

5. The composition of claim 1 wherein the base component is non-polymeric and has two or more CIM subgroups upon which the active agent is bonded.

6. The composition of claim 1 wherein the base component includes a plurality of said CIM subgroups on a polymeric backbone forming a matrix to which the active agent is leashed.

7. The composition of claim 4 wherein the active agent is capped by the base component.

8. The composition of claim 6 wherein the active agent is leashed to the base component.

9. The composition of claim 1 wherein each said CIM group includes one or more cyclic subgroups.

10. The composition of claim 1 wherein each said CIM group is noncyclic in structure.

11. The composition of claim 1 wherein said covalent bond is an orthoester-type linkage.

12. The composition of claim 1 where each said CIM group is selected from the aggregation comprising ketene acetals, vinyl ethers, ketene thioacetals and vinyl thioethers.

13. The composition of claim 1 wherein each said CIM group is a ketene acetal.

14. The composition of claim 1 wherein each said CIM group is a vinyl ether.

15. The composition of claim 1 wherein each said CIM group is a ketene thioacetal.

16. The composition of claim 1 wherein each said CIM group is a vinyl thioether.

17. The composition of claim 1 wherein each said PA group is an alcohol.

18. The composition of claim 1 wherein each said PA group is a phenol.

19. The composition of claim 1 wherein each said PA group is a carboxylic acid.

20. The composition of claim 1 wherein each said PA group is a thiol.

21. The composition of claim 1 wherein each said PA group is an amine.

22. The composition of claim 1 wherein each said PA group is an amide.

23. The composition of claim 1 wherein each said PA group is a urethane.

24. The composition of claim 1 wherein each said PA group is a phosphate ester.

25. The composition of claim 1 wherein each said PA group is a sulfonic acid.

26. The composition of claim 1 wherein each said PA group is an oxime.

27. The composition of claim 1 wherein the active agent includes exactly one PA group.

28. The composition of claim 1 wherein the active agent includes multiple PA groups, each of which is covalently bonded to a monomeric base group including a single CIM group.

29. The composition of claim 28 wherein said PA groups on the agent are selected from the same functional group class.

30. The composition of claim 28 wherein said PA groups on the agent are selected in any combination from the defined PA functional groups.

31. The composition of claim 1 wherein said CIM group is a ketene acetal, said PA group is an alcohol and said covalent bond is an orthoester linkage.

32. The composition of claim 1 wherein said CIM group is a vinyl ether with the alpha-vinyl ether carbon substituted with a hydrogen, said PA group is an alcohol and said convelent bond is an acetal linkage.

33. The composition of claim 1 wherein said CIM group is a vinyl ether with the alpha-vinyl ether carbon substituted with a hydrocarbon, said PA group is an alcohol and said covalent bond is a ketal linkage.

34. The composition of claim 2 wherein a substitution leading to an increase in the molecular weight of the base component generally results in increased hydrophobicity of said covalent bond and thus slows the rate of hydrolysis in a specified environment.

35. The composition of claim 1 wherein the covalent bond is destructible via hydrolysis at a predictable reaction rate in a specified environment to yield a hydrolytically degraded base component and the active agent component as separate molecules.

36. A method of creating an active chemical structure wherein the active portion thereof is adapted to be predictably released therefrom by hydrolysis, in steps comprising:
  A. selecting a carrier component;
  B. chemically treating the base carrier component such that one or more exposed CIM subgroups is created thereon, with a CIM subgroup being defined as a moiety capable of forming a hydrolyzable covalent bond by a carbonium ion mechanism with moieties including available hydrogen releasing polar groups;
  C. selecting an active agent component including a bondable PA subgroup, with a PA subgroup being defined as a moiety capable of forming a hydrolyzable covalent bond with one of said CIM groups; and
  D. reacting the active agent with said chemically treated carrier component so as to form a covalent orthoester-type linkage bonding between respective ones of said bondable PA groups and each said CIM subgroup.

37. The method of claim 36 wherein each said bondable PA subgroup is selected from the aggregation comprising alcohols, phenols, carboxylic acids, thiols, amines, amides, urethanes, phosphate esters, sulfonic acids and oximes.

38. The method of claim 36 wherein each said bondable CIM subgroup is noncyclic in structure.

39. The method of claim 36 wherein each said bondable CIM subgroup includes one or more cyclic components.

40. The method of claim 36 wherein the base carrier component is monomeric, includes a single one of said CIM subgroups and the active agent is capped thereto.

41. The method of claim 36 wherein the base component system is non-polymeric and has two or more CIM subgroups upon which the active agent is bonded.

42. The method of claim 36 wherein the base carrier component is polymeric in structure and includes a plurality of said CIM subgroups and the active agent is leashed thereto.

43. The method of claim 36 wherein said PA groups on the agent are selected from the same functional group class.

44. The method of claim 36 wherein said PA groups on the agent are selected in any combination from the defined PA functional groups.

45. The method of claim 36 wherein each said CIM subgroup is selected from the aggregation comprising ketene acetals, vinyl ethers, ketene thioacetals and vinyl thioethers.

* * * * *